United States Patent
Liu

(10) Patent No.: US 12,313,630 B2
(45) Date of Patent: May 27, 2025

(54) METHODS FOR DETERMINING CONCENTRATION OF LOW AND HIGH CONCENTRATION PROTEINS IN A SINGLE SAMPLE

(71) Applicant: ESSEN INSTRUMENTS, INC., Ann Arbor, MI (US)

(72) Inventor: Zhaoping Liu, Ann Arbor, MI (US)

(73) Assignee: SARTORIUS BIOANALYTICAL INSTRUMENTS, INC., Bohemia, NY (US)

( * ) Notice: Subject to any disclaimer, the term of this patent is extended or adjusted under 35 U.S.C. 154(b) by 766 days.

(21) Appl. No.: 17/255,012

(22) PCT Filed: Aug. 28, 2019

(86) PCT No.: PCT/US2019/048456
§ 371 (c)(1),
(2) Date: Dec. 22, 2020

(87) PCT Pub. No.: WO2020/047026
PCT Pub. Date: Mar. 5, 2020

(65) Prior Publication Data
US 2021/0270829 A1   Sep. 2, 2021

Related U.S. Application Data

(60) Provisional application No. 62/725,007, filed on Aug. 30, 2018.

(51) Int. Cl.
*G01N 33/543* (2006.01)
(52) U.S. Cl.
CPC . *G01N 33/54393* (2013.01); *G01N 2333/525* (2013.01); *G01N 2333/5406* (2013.01); *G01N 2333/57* (2013.01)
(58) Field of Classification Search
CPC ....... G01N 33/54393; G01N 2333/525; G01N 2333/5406; G01N 2333/57; G01N 33/58; G01N 2333/54; G01N 2333/5434
See application file for complete search history.

(56) References Cited

U.S. PATENT DOCUMENTS

| | | |
|---|---|---|
| 2005/0069958 A1 | 3/2005 | Mills |
| 2005/0202010 A1* | 9/2005 | Giroir ............... A61P 9/10 424/145.1 |
| 2009/0023144 A1 | 1/2009 | Sun |
| 2011/0312506 A1 | 12/2011 | Von Specht |
| 2012/0034209 A1* | 2/2012 | Perretti ............. A61P 17/06 424/139.1 |
| 2012/0135883 A1 | 5/2012 | Lehmann |
| 2013/0165335 A1 | 6/2013 | Lea |

FOREIGN PATENT DOCUMENTS

| | | | |
|---|---|---|---|
| WO | 2005/012505 | 2/2005 | |
| WO | WO-2005012505 A2 * | 2/2005 | ............ B82Y 15/00 |
| WO | 2005/084283 | 9/2005 | |
| WO | 2005/106482 | 11/2005 | |
| WO | WO-2005106482 A1 * | 11/2005 | ....... G01N 33/54306 |
| WO | 2007/067680 | 6/2007 | |
| WO | WO-2007067680 A2 * | 6/2007 | ....... G01N 33/54346 |
| WO | 2008/008858 | 1/2008 | |
| WO | 2011/102903 | 8/2011 | |
| WO | WO-2012051106 A1 * | 4/2012 | .......... A61K 31/785 |
| WO | 2013/071055 | 5/2013 | |
| WO | 2014/107480 | 7/2014 | |
| WO | WO-2014107480 A1 * | 7/2014 | ............ G01N 33/53 |
| WO | 2016/174106 | 11/2016 | |
| WO | 2017/102786 | 6/2017 | |

OTHER PUBLICATIONS

Valikangas et. al., A systematic evaluation of normalization methods in quantitative label-free proteomics. Briefings in Bioinformatics , 19(1), 2018, 1-11 (Year: 2016).*
Ara et. al., Interleukin-6 in the bone marrow microenvironment promotes the growth and survival of neuroblastoma cells. Cancer Res. Jan. 1, 2009; 69(1): 329-337 (Year: 2009).*
Cox ( "Immunoassay Methods" in "Assay Guidance Manual" 2012 by Markossian et al. editors) (Year: 2012).*
McDonald J. Immunol. Methods 2016 433:6-16 (Year: 2016).*
Klabusay (Mediators of Inflammation 2006 Article ID 65237, p. 1-7). (Year: 2006).*
The International Search Report (ISR) with Written Opinion for PCT/US2019/048456 dated Nov. 18, 2019, pp. 1-19.

* cited by examiner

*Primary Examiner* — Changhwa J Cheu
(74) *Attorney, Agent, or Firm* — MCDONNELL BOEHNEN HULBERT & BERGHOFF LLP

(57) ABSTRACT

Disclosed herein are methods for determining a concentration of at least one low concentration protein and at least one high concentration protein in a biological sample.

23 Claims, 1 Drawing Sheet

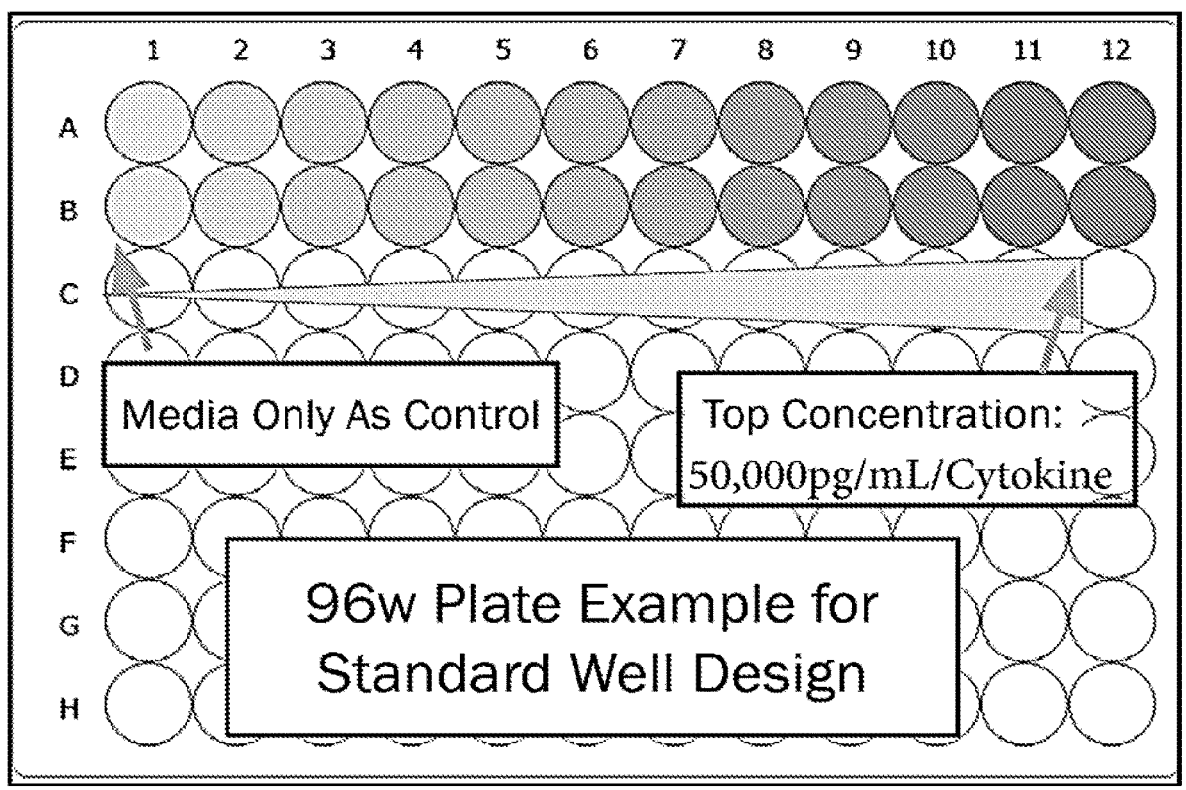

METHODS FOR DETERMINING CONCENTRATION OF LOW AND HIGH CONCENTRATION PROTEINS IN A SINGLE SAMPLE

CROSS REFERENCE

This application is a U.S. national phase of International Application No. PCT/US2019/048456, filed on Aug. 28, 2019, which claims priority to U.S. Provisional Application No. 62/725,007, filed Aug. 30, 2018, both of which are incorporated by reference herein in their entirety.

BACKGROUND

Current methods for determining the concentration of proteins in the same sample that are expressed at widely diverging levels (i.e.: at least 10-fold) are inadequate. Current methods require sample dilution to ensure highly secreted proteins are in the linear range of detection, but such dilution lowers the concentration of many low concentration analytes below the lower limit of detection.

SUMMARY

In a first aspect, the disclosure provides methods for determining a concentration of at least one low concentration protein and at least one high concentration protein in a biological sample, the method comprising:
  (a) in a plurality of sample wells in an assay plate, incubating (i) first capture reagents and (ii) the biological sample, wherein the first capture reagents comprises first binding molecules bound to a surface, wherein the first binding molecules selectively bind to the at least one low concentration protein, wherein the incubating is for a time and under conditions to promote binding of the at least one low concentration protein in the biological sample to the first binding molecules to produce a first binding mixture in each of the sample wells, wherein each sample well has a first sample well volume;
  (b) in each of the sample wells, mixing the first binding mixture with second capture reagents, wherein the second capture reagents comprises second binding molecules bound to a surface, wherein the second binding molecules selectively bind to the at least one high concentration protein, wherein the mixing is for a time and under conditions to promote binding of the at least one high concentration protein in the biological sample to the second binding molecules to produce a second binding mixture in each of the sample wells, wherein the mixing comprises increasing volume in each sample well to produce a second sample well volume that is at least ten-fold higher than the first sample well volume, wherein the at least one high concentration protein is expected to be present in the biological sample in a concentration at least ten-fold greater than an expected concentration of the at least one low concentration protein; and
  (c) determining a concentration of the at least one low concentration protein and the at least one high concentration protein in the biological sample.

In one embodiment, the assay plate comprises two or more control wells, wherein the method further comprises:
  (d) incubating in the two or more control wells (i) the first capture reagents and (ii) an protein standard comprising a known amount of the at least one low concentration protein and the at least one high concentration protein, wherein the incubating is for a time and under conditions to promote binding of the low concentration protein in the protein standard to the first binding molecules to produce a first control binding mixture in each of the control wells, wherein each control well has a first control well volume;
  (e) in each of the two or more control wells, incubating the first control binding mixture with the second capture reagents for a time and under conditions to promote binding of the high concentration protein in the protein standard to the second binding molecules to produce a second control binding mixture in each of the control wells, wherein the mixing comprises increasing the volume in each control well to produce a second control well volume that is at least ten-fold higher than the first control well volume;
  (f) determining the concentration of the at least one low concentration protein and the at least one high concentration protein in the second control binding mixture in each control well; and
  (g) normalizing the determined concentration of the at least one low concentration protein and the at least one high concentration protein in second binding mixture in each sample well based on the concentration of the at least one low concentration protein and the at least one high concentration protein in the second control binding mixture in each control well.

In another embodiment, different controls wells of the two or more control wells comprise protein samples having different concentrations of the low concentration protein and different concentrations of the high concentration protein.

In a further embodiment, determining the amount of the at least one low concentration protein and the at least one high concentration protein in the second binding mixture in each sample well comprises:
  (i) contacting the second binding mixture in each sample well with a detection reagent, wherein the detection reagent binds to the binding molecules present in the first capture reagents and the binding molecules in the second capture reagents, wherein the contacting is done for a time and under conditions for binding of the detection reagent to the binding molecules present in the first capture reagents and the binding molecules in the second capture reagents produce a detectable protein mixture; and
  (ii) detecting the detectable protein mixture in each sample well to determine the amount of the at least one low concentration protein and the at least one high concentration protein.

In various embodiments, the biological sample comprises cells in cell culture medium or cellular protein extracts. In another embodiment, the at least one low concentration protein is one or more protein selected from the group consisting of interleukin 4 (IL-4), interleukin 6 (IL-6), interleukin 12 (IL-12), interleukin 17A (IL-17A), soluble Fas, and Granulocyte-macrophage colony-stimulating factor (GM-CSF). In a further embodiment, the at least one high concentration protein is one or more protein selected from the group consisting of interferon gamma (INF-gamma), tumor necrosis factor alpha (TNF-alpha), Granzyme B, interleukin 2 (IL-2), and interleukin (IL-6).

In one embodiment, the at least one low concentration protein comprises IL-17A, and the at least one high concentration protein comprises IFN gamma. In another embodiment, the biological sample comprises T cells in cell culture medium, or a T cell protein extract.

In another embodiment, the at least one low concentration protein comprises IL-6, and the at least one high concentration protein comprises IFN gamma and TNF alpha. In a further embodiment, the biological sample comprises T cells in cell culture medium, or a T cell protein extract.

In one embodiment, the at least one low concentration protein comprises sFas, and the at least one high concentration protein comprises Granzyme B. In another embodiment, the biological sample comprises T cells in cell culture medium, or a T cell protein extract.

In one embodiment, the at least one low concentration protein comprises IL-4, and the at least one high concentration protein comprises IL-2 and TNF alpha. In another embodiment, the biological sample comprises B cells in cell culture medium, or a B cell protein extract.

In one embodiment, the at least one low concentration protein comprises IL-12, and the at least one high concentration protein comprises TNF alpha. In another embodiment, the biological sample comprises macrophages in cell culture medium, or a macrophage protein extract.

In one embodiment, the at least one low concentration protein comprises GM-CSF, and the at least one high concentration protein comprises IL-6. In another embodiment, the biological sample comprises bone marrow cells in cell culture medium, or a bone marrow cell protein extract.

In one embodiment, the first binding molecules and the second binding molecules comprise antibodies. In another embodiment, the surface of the first capture reagents comprise beads, and the surface of the second capture reagents comprise beads. In a further embodiment, the mixing comprises increasing the volume in each sample well to produce a second sample well volume that is between 10-fold and 100-fold higher than the first sample well volume. In another embodiment, the determining an amount of the at least one low concentration protein and the at least one high concentration protein in the second binding mixtures in each sample well is carried out by flow cytometry.

In another aspect, the disclosure provides kits comprising first capture reagents, second capture reagents, and detection reagents as disclosed herein in any embodiment or combination of embodiments.

DESCRIPTION OF THE FIGURES

FIG. 1 is a schematic depiction of an arrangement of standard wells from left to right (from low concentration to high concentration) in a 96-well plate.

DETAILED DESCRIPTION

All references cited are herein incorporated by reference in their entirety.

As used herein, the singular forms "a". "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

Unless the context clearly requires otherwise, throughout the description and the claims, the words 'comprise'. 'comprising', and the like are to be construed in an inclusive sense as opposed to an exclusive or exhaustive sense: that is to say, in the sense of "including, but not limited to". Words using the singular or plural number also include the plural and singular number, respectively. Additionally, the words "herein." "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect are provided methods for determining a concentration of at least one low concentration protein and at least one high concentration protein in a biological sample, the method comprising:

(a) in a plurality of sample wells in an assay plate, incubating (i) first capture reagents and (ii) the biological sample, wherein the first capture reagents comprises first binding molecules bound to a surface, wherein the first binding molecules selectively bind to the at least one low concentration protein, wherein the incubating is for a time and under conditions to promote binding of the at least one low concentration protein in the biological sample to the first binding molecules to produce a first binding mixture in each of the sample wells, wherein each sample well has a first sample well volume;

(b) in each of the sample wells, mixing the first binding mixture with second capture reagents, wherein the second capture reagents comprises second binding molecules bound to a surface, wherein the second binding molecules selectively bind to the at least one high concentration protein, wherein the mixing is for a time and under conditions to promote binding of the at least one high concentration protein in the biological sample to the second binding molecules to produce a second binding mixture in each of the sample wells, wherein the mixing comprises increasing volume in each sample well to produce a second sample well volume that is at least ten-fold higher than the first sample well volume, wherein the at least one high concentration protein is expected to be present in the biological sample in a concentration at least ten-fold greater than an expected concentration of the at least one low concentration protein; and (c) determining a concentration of the at least one low concentration protein and the at least one high concentration protein in the biological sample.

Current methods for determining the concentration of proteins in the same sample that are expressed at widely diverging levels (i.e.: at least 10-fold) are inadequate. The methods disclosed herein provide a significant improvement over prior methods, and permits additional multiplex analysis. The methods contribute to ease of use by greatly accelerating workflow by using a single assay to measure secreted proteins with wide concentration ranges and reduces reagent consumption. Protein capture, detection and quantitation can be done in the same sample well.

The biological samples include proteins that are expected to be expressed at low and high levels, wherein the at least one high concentration protein is expected to be present in the biological sample (i.e.: secreted from cells or present in cell/protein extracts) in a concentration at least ten-fold greater than an expected concentration of the at least one low concentration protein. In various embodiments, the at least one high concentration protein is present in the biological sample in a concentration at least 10, 15, 20, 25, 30, 35, 40, 45, 50, 55, 60, 65, 70, 75, 80, 85, 90, 95, 100, 125, 150, 175, 200, 225, or 250-fold greater than the concentration of the at least one low concentration protein. The at least one low concentration protein may be 1, 2, 3, 4, 5, or more low concentration proteins. Similarly, the at least one high concentration protein may be 1, 2, 3, 4, 5, or more high concentration proteins. The at least one low and at least one high concentration protein may be any proteins meeting the requirements herein for low and high concentration proteins that a user wants to determine a concentration of. In various non-limiting embodiments, the at least one low concentration protein is one or more protein selected from the group consisting of interleukin 4 (IL-4), interleukin 6 (IL-6), interleukin 12 (IL-12), interleukin 17A (IL-17A), soluble Fas, and Granulocyte-macrophage colony-stimulating factor (GM-CSF). In various further embodiments, the at least one high concentration protein is one or more protein selected from the group consisting of interferon gamma (INF-gamma), tumor necrosis factor alpha (TNF-alpha). Granzyme B, interleukin 2 (IL-2), and interleukin (IL-6)

Any suitable biological sample that expresses both low concentration and high concentration proteins (as defined herein) can be used, including but not limited to isolated cells (including but not limited to B cells, T cells, macrophages, and bone marrow cells), cell supernatants, cell extracts thereof, serum, serum extracts, biological fluids (including but not limited to blood), and biological fluid extracts (including but not limited to blood extracts). In one specific embodiment, the biological sample comprises cells in cell culture medium. In another specific embodiment, the biological sample comprises cellular protein extracts.

In various specific embodiments that may be combined or separate:
(a) wherein the at least one low concentration protein comprises IL-17A, and the at least one high concentration protein comprises IFN gamma: in one such embodiment, the biological sample comprises T cells in cell culture medium, or a T cell protein extract;
(b) the at least one low concentration protein comprises IL-6, and the at least one high concentration protein comprises IFN gamma and TNF alpha: in one such embodiment, the biological sample comprises T cells in cell culture medium, or a T cell protein extract;
(c) the at least one low concentration protein comprises sFas, and the at least one high concentration protein comprises Granzyme B: in one such embodiment, the biological sample comprises T cells in cell culture medium, or a T cell protein extract;
(d) the at least one low concentration protein comprises IL-4, and the at least one high concentration protein comprises IL-2 and TNF alpha: in one such embodiment, the biological sample comprises B cells in cell culture medium, or a B cell protein extract;
(e) the at least one low concentration protein comprises IL-12, and the at least one high concentration protein comprises TNF alpha: in one such embodiment, the biological sample comprises macrophages in cell culture medium, or a macrophage protein extract;
(f) the at least one low concentration protein comprises GM-CSF, and the at least one high concentration protein comprises IL-6; in one such embodiment, the biological sample comprises bone marrow cells in cell culture medium, or a bone marrow cell protein extract;

The biological sample may be of any origin, including but not limited to human, rodent (i.e., mouse, rat, hamster, etc.), rabbit, pig, goat, monkey, sheep, horse, bovine, etc. In one specific embodiment, the biological sample is of human origin.

The methods are carried out in a plurality of sample wells on an assay plate (including but not limited to a micro-titer plate). Thus, the methods can be carried out in 2, 3, 4, 5, 6, 7, 8, 9, 10, 15, 20, 24, 30, 36, 40, 48, 50, 60, 70, 75, 80, 90, 96, or more wells as deemed suitable by a user.

The methods use capture reagents to bind to the low concentration proteins (first capture reagent) or high concentration proteins (second capture reagent) present in the biological sample. The capture reagents comprise binding molecules that selectively bind to the at least one low concentration protein (first binding molecules) or at least one high concentration protein (second binding molecules). It will be understood that if two different low concentration proteins are to be measured from a given biological sample, then there will be two different populations of first binding molecules (i.e.: first binding molecules for low concentration protein 1 and first binding molecules for low concentration protein 2). Similarly, if two different high concentration proteins are to be measured from a given biological sample, then there will be two different populations of second binding molecules (i.e.: second binding molecules for high concentration protein 1 and second binding molecules for high concentration protein 2). Any suitable binding molecules can be used that selectively bind to a low concentration protein or a high concentration protein. In various non-limiting embodiments, the binding molecules comprise antibodies, affimers, aptamers, or other protein/sugar/lipid or combination molecules. In one specific embodiment, the first and second binding molecules comprise antibodies that selectively bind to a low concentration protein or a high concentration protein. Such selective antibodies are commercially available from a number of vendors, including BD Biosciences. Sigma Chemical Company, Millipore, and ThermoFisher Scientific.

The first and second binding molecules in the first and second capture reagents are bound to a surface. Any suitable surface can be used, including but not limited to glass, cellulose, polyacrylamide, nylon, polystyrene, polyvinyl chloride, polypropylene supports, magnetic or paramagnetic beads, agarose beads, and filtration media such as NHS-activated Sepharose or CNBr-activated Sepharose. In one specific embodiment, the binding molecules in the capture reagents are bound to a bead, such as a magnetic or paramagnetic bead, or a non-magnetic bead. In one embodiment, the bead is a non-magnetic bead including but not limited to a polystyrene bead. Such polystyrene beads may be of any suitable size, including but not limited to between 5-10, 6-9, 7-8, or about 7 μm in diameter. A magnetic or paramagnetic capture bead is typically about 1 mm in diameter or less, and is sufficiently small enough in order to prevent sedimentation or clogging. Suitable beads can be obtained from different sources (e.g., Dynabeads My-One™ from Invitrogen Dynal, Norway or Estapore from Merck, France). Beads can be pre-coupled or coated with binding molecules for passive or active coupling of antibodies or antigens. In other embodiments, the capture bead can be an agarose bead. Typically agarose beads are about 20 μm to 350 μm in diameter. In another specific embodiment, the binding molecules in the capture reagents are present in a printed array in the wells of a micro-titer plate.

Any suitable density of capture reagents can be used in the assays. In one non-limiting embodiment, each population of capture reagent specific for a low or high concentration protein is present at a density of between about 0.01 million to about 100 million capture reagents per milliliter. In various further embodiments, each population of capture reagents is present at a density of between about 0.1 million to about 50 million, between about 0.25 million to about 25 million, between about 0.5 million to about 10 million, or between about 0.75 million to about 5 million capture reagents per milliliter.

The incubating, mixing, and contacting steps are carried out for a time and under conditions to promote the recited binding events. Any suitable conditions to promote such incubating, mixing, and contacting may be used, and it is within the level of those of skill in the art to determine such appropriate conditions as temperature, length of incubation, application of stirring or other mixing forces, medium to be used, wash steps to incorporate, etc., based on the teachings herein. Non-limiting embodiments are described in detail herein.

The first binding molecules bind to the at least one low concentration protein in the biological sample to produce a first binding mixture in each of the sample wells, wherein each sample well has a first sample well volume. Subsequently, in the same sample wells, the first binding mixture is mixed with second capture reagents, and the second binding molecules bind to the at least one high concentration protein in the biological sample to produce a second binding mixture in each of the sample wells. The mixing comprises increasing volume in each sample well (i.e.: the first sample well volume) to produce a second sample well volume that is at least ten-fold higher than the first sample well volume. This dilution step after capture of the low concentration proteins permits significantly improved dynamic range for determining concentration of the at least one high concentration protein in the biological sample. In various embodiments, the increase in the second sample well volume may be at least 10, 15, 20, 25, 30, 35, 40, 45, 50, 75, 100, 125, 150, 200, or 250-fold relative to the first sample well volume, as deemed appropriate by a user based on the teachings herein.

The methods then comprise determining a concentration of the at least one low concentration protein and the at least one high concentration protein in the biological sample. In one embodiment, the determining step comprises (d) contacting the second binding mixture in each sample well with a detection reagent, wherein the detection reagent binds to the binding molecules present in the first capture reagents and the binding molecules in the second capture reagents, wherein the contacting is done for a time and under conditions for binding of the detection reagent to the binding molecules present in the first capture reagents and the binding molecules in the second capture reagents produce a detectable protein mixture; and (e) detecting the detectable protein mixture in each sample well to determine the amount of the at least one low concentration protein and the at least one high concentration protein.

Any suitable technique for detecting the detectable protein mixture can be used, depending on the detectable label employed, including but not limited to enzyme-linked immunosorbent assays (ELISA), flow cytometry, plate reader, Meso Scale Discovery platform, and fluorescent microscopy. Any suitable detectable label may be used, including but not limited to a fluorescent label, hapten, colorimetric label, various radioactive labels, enzymes, prosthetic groups, fluorescent markers, luminescent markers, bioluminescent markers, labeled particles such as silicon, glass, or metal particles; protein-protein binding pairs, protein-antibody binding pairs and the like. Examples of fluorescent labels include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, allophycocyanin (APC), brilliant violet dye, brilliant ultraviolet dye, and phycoerythrin. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Detectable labels are commercially available from a variety of sources. In certain embodiments the detection label comprises a fluorophore or fluorescent protein.

In one specific embodiment, the detection involves flow cytometry, by suspending the relevant binding complexes in a stream of fluid and passing them by an electronic detection apparatus, allowing simultaneous multi-parametric analysis of the physical and chemical characteristics of up to tens of thousands of complexes per second.

In one embodiment where the first and second binding molecules comprise antibodies, the detection reagents may comprise detectably labeled target secondary antibodies, or fragments thereof that retain the ability to bind to the first and second binding molecule antibodies. In various embodiments, the detection reagents comprise 2, 3, 4, 5, or more separately detectable labeled secondary antibodies, or fragments thereof, depending on the number of low concentration and high concentration proteins to be assessed. Such secondary antibodies are commercially available from a number of vendors, including BD Biosciences, Sigma Chemical Company, Millipore, and ThermoFisher Scientific.

In one embodiment, the assay plate comprises two or more control wells, wherein the method further comprises:

(d) incubating in the two or more control wells (i) the first capture reagents and (ii) an protein standard comprising a known amount of the at least one low concentration protein and the at least one high concentration protein, wherein the incubating is for a time and under conditions to promote binding of the low concentration protein in the protein standard to the first binding molecules to produce a first control binding mixture in each of the control wells, wherein each control well has a first control well volume;

(e) in each of the two or more control wells, incubating the first control binding mixture with the second capture reagents for a time and under conditions to promote binding of the high concentration protein in the protein standard to the second binding molecules to produce a second control binding mixture in each of the control wells, wherein the mixing comprises increasing the volume in each control well to produce a second control well volume that is at least ten-fold higher than the first control well volume;

(f) determining the concentration of the at least one low concentration protein and the at least one high concentration protein in the second control binding mixture in each control well; and (g) normalizing the determined concentration of the at least one low concentration protein and the at least one high concentration protein in second binding mixture in each sample well based on the concentration of the at least one low concentration protein and the at least one high concentration protein in the second control binding mixture in each control well.

Steps (d)-(f) correspond to steps (a)-(c) above, only being carried out in one or more (2, 3, 4, 5, 6, 7, 8, 9, 10, or more) control wells and using protein standards for the low and high concentration proteins to be assayed, rather than a biological sample. A normalizing step is then added to normalize the determined concentration of the at least one low concentration protein and the at least one high concentration protein in second binding mixture in each sample well based on the concentration of the at least one low concentration protein and the at least one high concentration protein in the second control binding mixture. Any suitable normalizing process may be used, including those disclosed in detail herein. In one embodiment, different controls wells of the two or more control wells comprise protein samples having different concentrations of the low concentration protein and different concentrations of the high concentration protein. In one embodiment, the normalizing comprises generating a standard curve for each low and high concentration protein in the protein standard, wherein the concentration of the low and high concentration proteins in each biological sample is measured by reference to the standard curve for each low and high concentration protein in the protein standard.

In other embodiments, the methods can be multiplexed with additional cell characterization and functional assays. In various non-limiting embodiments, such additional cell characterization and functional assays include, but are not limited to, T-cell identity and characterization, cell viability, apoptosis, cell number, and cell surface biomarker assays. For example, the sample wells may be contacted with a detectable cell viability dye, cell surface biomarker, or marker of apoptosis. For example, T cell and B cell surface markers identify their lineage and stage in the differentiation process.

In another aspect are disclosed kits that comprise:
(a) first capture reagents as described in any embodiment or combination of embodiments herein;
(b) second capture reagents as described in any embodiment or combination of embodiments herein; and
(c) detection reagents as described in in any embodiment or combination of embodiments herein.

The kits may further comprise any other reagent disclosed herein or additional useful tools for carrying out the methods, including but not limited to protein standards, detectable labels, assay plates, buffers, etc.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Examples

Protein Standard

Protein standards (IFNg, TNFa, and IL-4) were mixed into a single 1.5 ml centrifuge tube to generate a protein standard. 200 µL of fresh culture media (RPMI 1640 with 10% fetal bovine serum, from VWR) was added to the tube with the protein standards and mixed. Serial 1:3 dilutions into cell culture medium of the protein standard were prepared.

Capture Reagent Preparation

First capture reagent (low concentration protein): 24 uL of IL-4 capture beads (polystyrene beads covalently conjugated with anti-IL-4 antibody) (QBeads™ kit (IntelliCyt)) were diluted with 1.2 mls of buffer (0.1% bovine serum albumin in phosphate-buffered saline) and mixed.

Second capture reagent (high concentration protein): 24 uL of IFNγ capture beads (polystyrene beads covalently conjugated with anti-IFNγ antibody) (QBeads™ kit (IntelliCyt)) and 24 uL of TNFα capture beads (polystyrene beads covalently conjugated with anti-TNFα antibody) (QBeads™ kit (IntelliCyt)) were diluted with 1.2 mls of buffer and mixed. The mixture was then dilute with a 17-fold volume of fresh cell culture media (RPMI 1640 with 10% fetal bovine serum, from VWR).

The IL-4 capture bead mixture was vortexed and transferred to a reservoir. To the bottom of each well. 10 uL of the IL-4 capture bead mix (approximately 0.12 million capture beads/mL) was added to the assay plate. The beads were agitated in the reservoir occasionally during the transfer of the beads to the plate to prevent the beads from settling. 10 µL cytokine protein standards of various concentrations were added to each well of the assay plate designated for Standards (control wells) (For example, see FIG. 1 below).

The plate was spun at 300 g for 5 seconds to ensure that all samples are at the well bottom and not attached to the well sides. The plate was then mixed for 20 seconds at 2,000 rpm (iQue™ plate shaker. Intellicyt)) to ensure thorough mixing. A lid was placed on the plate and the plate was incubated at room temperature for 60 minutes without light.

The pre-diluted pre-mixed IFNγ/TNFα capture beads were vortexed to mix and 180 µL of the suspension (0.013 million beads/mL) was added each sample well. The beads were agitated occasionally during the transfer of the beads from the reservoir to the plate to prevent the beads from settling. A lid was placed on the plate and the plate was incubated at room temperature for 60 minutes without light. No shaking of the plate was carried out at this step due to the volume of liquid in the sample wells.

After incubation, the plate was spun at 300 g for 5 minutes. The supernatant was aspirated with a BioTek™ plate washer (ELx405 model), following the manufacturer's recommendation. The sample in the residue liquid in the plate was agitated on the iQue™ plate shaker at 3,000 rpm for 60 seconds.

10 µL of IL-4/IFNg/TNFα detection reagent (cytokine detection cocktail available from a variety of suppliers) was added to each well. The detection reagent comprises Phycoerythrin (PE)-conjugated antibody against the binding molecules present in the first capture reagents (sandwich immunoassay), and the PE-conjugated antibody against the binding molecules present in the second capture reagents. The plate was spun at 300 g for 5 seconds to ensure that all samples were at the well bottom and not attached to the well sides. The plate was then mixed for 20 seconds at 2,000 rpm using an iQue™ plate shaker to ensure thorough mixing. The assay plate was covered with a lid and incubated at room temperature for 120 minutes without light.

100 µL of wash buffer was added to each well. The assay plate was spun at 300 g, for 5 minutes. The supernatant was aspirated with a BioTek™ plate washer (ELx405 model) following the manufacturer's recommendation. The sample in the residue liquid was agitated in the well at 3,000 rpm for 60 seconds using an iQue™ plate shaker. 20 µL wash buffer was added to each well, and the plate was gently tapped on a bench to ensure that all samples were at the well bottom and not attached to the well sides.

Sample acquisition was carried out on an iQue™ Screener PLUS (VBR) system (Intellicyt), and data were analyzed by IntelliCyt's ForeCyt™ software.

Results

The results are shown in FIGS. 2 and 3, and demonstrate the linear range of the standard curves and the basic the distribution of the input standard concentration and the output fluorescence signal unit. For IFNg, the linear range is between 91-22.204 pg/mL (compared to 8-1628 pg/ml using previous methods); for TNFa the linear range is 181-50,000 pg/mL (compared to 12-5831 pg/ml using previous methods); for IL-4, the linear range is between 8-6,759 pg/mL. Compared with previous methods, the linear range of IFNg and TNFa is shifted to a significantly higher end, which enables the quantification of highly secreted IFNg and TNFa proteins in the sample. The IL-4 linear range allows the quantification of the weakly secreted IL-4 proteins to as low as 8 pg/mL in the same sample. All these results suggest the methods disclosed herein provide significant improvements in simultaneously detecting and quantifying high concentrated secreted proteins as well as low concentration secreted proteins in the same assay.

I claim:

1. A method for determining a concentration of at least one low concentration protein and at least one high concentration protein in a biological sample, the method comprising:
   (a) in a plurality of sample wells in an assay plate, incubating (i) first capture reagents and (ii) the biological sample, wherein the first capture reagents comprise first antibodies bound to a surface, wherein the first antibodies selectively bind to the at least one low concentration protein, wherein the incubating is for a time and under conditions to promote binding of the at least one low concentration protein in the biological sample to the first antibodies to produce a first binding mixture in each of the sample wells, wherein each sample well has a first sample well volume;
   (b) in each of the sample wells, mixing the first binding mixture with second capture reagents, wherein the second capture reagents comprise second antibodies bound to a surface, wherein the second antibodies selectively bind to the at least one high concentration protein, wherein the mixing is for a time and under conditions to promote binding of the at least one high concentration protein in the biological sample to the second antibodies to produce a second binding mixture in each of the sample wells, wherein the mixing comprises increasing volume in each sample well to produce a second sample well volume that is at least ten-fold higher than the first sample well volume, wherein the at least one high concentration protein is expected to be present in the biological sample in a concentration at least ten-fold greater than an expected concentration of the at least one low concentration protein; and
   (c) determining a concentration of the at least one low concentration protein and the at least one high concentration protein in the biological sample.

2. The method of claim 1, wherein the assay plate comprises two or more control wells, wherein the method further comprises:
   (d) incubating in the two or more control wells (i) the first capture reagents and (ii) an protein standard comprising a known amount of the at least one low concentration protein and the at least one high concentration protein, wherein the incubating is for a time and under conditions to promote binding of the low concentration protein in the protein standard to the first antibodies to produce a first control binding mixture in each of the control wells, wherein each control well has a first control well volume;
   (e) in each of the two or more control wells, incubating the first control binding mixture with the second capture reagents for a time and under conditions to promote binding of the high concentration protein in the protein standard to the second antibodies to produce a second control binding mixture in each of the control wells, wherein the mixing comprises increasing the volume in each control well to produce a second control well volume that is at least ten-fold higher than the first control well volume;
   (f) determining the concentration of the at least one low concentration protein and the at least one high concentration protein in the second control binding mixture in each control well; and
   (g) normalizing the determined concentration of the at least one low concentration protein and the at least one high concentration protein in second binding mixture in each sample well based on the concentration of the at least one low concentration protein and the at least one high concentration protein in the second control binding mixture in each control well.

3. The method of claim 2, wherein different controls wells of the two or more control wells comprise protein samples having different concentrations of the low concentration protein and different concentrations of the high concentration protein.

4. The method of claim 1, wherein determining the amount of the at least one low concentration protein and the at least one high concentration protein in the second binding mixture in each sample well comprises:
   (i) contacting the second binding mixture in each sample well with a detection reagent, wherein the detection reagent binds to the antibodies present in the first capture reagents and the antibodies in the second capture reagents, wherein the contacting is done for a time and under conditions for binding of the detection reagent to the antibodies present in the first capture reagents and the antibodies in the second capture reagents produce a detectable protein mixture; and
   (ii) detecting the detectable protein mixture in each sample well to determine the amount of the at least one low concentration protein and the at least one high concentration protein.

5. The method of claim 1, wherein the biological sample comprises cells in cell culture medium, or wherein the biological sample comprises cellular protein extracts.

6. The method of claim 1, wherein the at least one low concentration protein is one or more protein selected from the group consisting of interleukin 4 (IL-4), interleukin 6 (IL-6), interleukin 12 (IL-12), interleukin 17A (IL-17A), and soluble Fas.

7. The method of claim 1, wherein the at least one high concentration protein is one or more protein selected from the group consisting of interferon gamma (INF-gamma), tumor necrosis factor alpha (TNF-alpha), Granzyme B, and interleukin 2 (IL-2).

8. The method of claim 1, wherein the at least one low concentration protein comprises IL-17A, and the at least one high concentration protein comprises IFN gamma.

9. The method of claim 8, wherein the biological sample comprises T cells in cell culture medium, or a T cell protein extract.

10. The method of claim 1, wherein the at least one low concentration protein comprises IL-6, and the at least one high concentration protein comprises IFN gamma and TNF alpha.

11. The method of claim 10, wherein the biological sample comprises T cells in cell culture medium, or a T cell protein extract.

12. The method of claim 1, wherein the at least one low concentration protein comprises sFas, and the at least one high concentration protein comprises Granzyme B.

13. The method of claim 12, wherein the biological sample comprises T cells in cell culture medium, or a T cell protein extract.

14. The method of claim 1, wherein the at least one low concentration protein comprises IL-4, and the at least one high concentration protein comprises IL-2 and TNF alpha.

15. The method of claim 14, wherein the biological sample comprises B cells in cell culture medium, or a B cell protein extract.

16. The method of claim 1, wherein the at least one low concentration protein comprises IL-12, and the at least one high concentration protein comprises TNF alpha.

17. The method of claim 16, wherein the biological sample comprises macrophages in cell culture medium, or a macrophage protein extract.

18. The method of claim 1, wherein the at least one low concentration protein comprises GM-CSF, and the at least one high concentration protein comprises IL-6.

19. The method of claim 18, wherein the biological sample comprises bone marrow cells in cell culture medium, or a bone marrow cell protein extract.

20. The method of claim 1, wherein the surface of the first capture reagents comprise beads, and the surface of the second capture reagents comprise beads.

21. The method of claim 1, wherein the mixing comprises increasing the volume in each sample well to produce a second sample well volume that is between 10-fold and 100-fold higher than the first sample well volume.

22. The method of claim 1, wherein the determining an amount of the at least one low concentration protein and the at least one high concentration protein in the second binding mixtures in each sample well is carried out by flow cytometry.

23. The method of claim 1, wherein:
(i) the at least one low concentration protein is IL-4, and the at least one high concentration protein is INF-gamma;
(ii) the at least one low concentration protein is IL-4, and the at least one high concentration protein is TNF-alpha;
(iii) the at least one low concentration protein is IL-4, and the at least one high concentration protein is IL-2;
(iv) the at least one low concentration protein is IL-6, and the at least one high concentration protein is INF-gamma;
(v) the at least one low concentration protein is IL-6, and the at least one high concentration protein is TNF-alpha;
(vi) the at least one low concentration protein is IL-6, and the at least one high concentration protein is IL-2;
(vii) the at least one low concentration protein is IL-17A, and the at least one high concentration protein is INF-gamma;
(viii) the at least one low concentration protein is IL-17A, and the at least one high concentration protein is TNF-alpha; or
(ix) the at least one low concentration protein is IL-17A, and the at least one high concentration protein is IL-2.

* * * * *